US007452557B2

(12) United States Patent
Yoshida

(10) Patent No.: US 7,452,557 B2
(45) Date of Patent: *Nov. 18, 2008

(54) PREVENTIVE OR THERAPEUTIC AGENT FOR POLLEN ALLERGY, ALLERGIC RHINITIS, ATOPIC DERMATITIS, ASTHMA OR URTICARIA, OR HEALTH FOOD FOR PREVENTION OR IMPROVEMENT OR REDUCTION OF SYMPTOMS THEREOF

(75) Inventor: Satoshi Yoshida, Tokyo (JP)

(73) Assignee: Original Image Co., Ltd., Kanagawa (JP)

( * ) Notice: Subject to any disclaimer, the term of this patent is extended or adjusted under 35 U.S.C. 154(b) by 482 days.

This patent is subject to a terminal disclaimer.

(21) Appl. No.: 10/964,750

(22) Filed: Oct. 15, 2004

(65) Prior Publication Data

US 2005/0100616 A1    May 12, 2005

Related U.S. Application Data

(62) Division of application No. 10/126,779, filed on Apr. 22, 2002, now Pat. No. 6,811,796.

(51) Int. Cl.
*A61K 36/68* (2006.01)
*A61K 36/9068* (2006.01)
*A61K 36/484* (2006.01)
*A61K 36/9066* (2006.01)
*A61K 36/899* (2006.01)
*A61K 36/286* (2006.01)

(52) U.S. Cl. .................. 424/738; 424/756; 424/757; 424/758; 424/774; 424/776; 424/778

(58) Field of Classification Search .............. 424/738, 424/758, 764, 776, 778, 439; 514/826, 861, 514/863
See application file for complete search history.

(56) References Cited

U.S. PATENT DOCUMENTS

| | | | |
|---|---|---|---|
| 4,749,690 A * | 6/1988 | Goldstein | |
| 5,401,777 A | 3/1995 | Ammon et al. | |
| 5,653,997 A | 8/1997 | Renimel et al. | |
| 5,696,273 A | 12/1997 | Andre et al. | |
| 6,258,816 B1 | 7/2001 | Singh et al. | |
| 6,482,421 B2 | 11/2002 | Weidner | |
| 6,811,796 B2 * | 11/2004 | Yoshida | |

FOREIGN PATENT DOCUMENTS

| | | |
|---|---|---|
| CN | 1112014 A | 11/1995 |
| CN | 1219413 A | 6/1999 |
| JP | 61291524 A | 12/1986 |
| JP | 02154655 A | 6/1990 |
| JP | 02225491 A | 9/1990 |
| JP | 06211673 A | 8/1994 |
| JP | 09020672 A | 1/1997 |
| JP | 09291299 | 11/1997 |
| JP | 10036279 A | 2/1998 |
| JP | 10120583 A | 5/1998 |
| JP | 10-236944 | 9/1998 |
| JP | 10-279491 | 10/1998 |
| JP | 11056297 A | 3/1999 |
| JP | 11116498 A | 4/1999 |
| JP | 11199550 A | 7/1999 |
| JP | 2000-014354 | 1/2000 |
| JP | 2000014354 A | 1/2000 |
| JP | 2001299273 A | 10/2001 |

OTHER PUBLICATIONS

Japanese language newspaper article *Yu-Kan Fuji*, published Jan. 24, 2002.
Imaoka et al., Wakan Iyakugau (1995), 12(3): 257:63. Chinese herbal medicines capable of IgE antibody suppression and interferon induction (Abstract).
Seki et al., Toho Igakkai Zasshi (1979), 26(3): 304-26. Experimental and clinical studies on lecithin-bound iodine with licorice as remedies for bronchial asthma (Abstract).
Kim et al., Archives of Pharmaceutical Research (1996), 19(2): 137-142. The effects of plantago-mucilage from the seeds of *Plantago asiatica* on the immune responses in ICR mice.
Murav'ev, Piatigorski Inst. Far., ZSRR, Pyatigorsk, USSR (1967), 23(7-8): 559-66. Chemical composition and technology of licorice and its preparations.
Imaoka et al., "Effect of Celosia Argentea and Cucurbita Moschata Extracts on Anti-DNP IgE Antibody Production in Mice," *Allergy*, 43(5):652-659, 1994.
Kakimoto et al., "Anti-Inflammatory and Anti-Allergic Effects of a Preparation of Crude Drugs, a Remedy for Nasal Disease (Fujibitol)," *Ouyou Yakuri*, 28(4): 555-565, 1984.
Toyoda et al., "Profiles of Potentially Antiallergic Flavonoids in 27 Kinds of Health Tea and Green Tea Infusions," *J. Agric. Food Chem.*, 45:2561-2564, 1997.
Nishibe, "Bioactive Phenolic Compounds in Traditional Medicines," *Pure & Appl. Chem.*, 66(10/11): 2263-2266, 1994.
Nishibe et al., "Bioactive Phenolic Compounds of Plantago Herb," *Foods Food Ingredients J.*, 166:43-49, 1995.
Nagase, "Adaptation to Treating Adult Grave Atopic Dermatitis on Chinese Herbal Composition," *Chul Rinsho*, 22(3): 32-34, 2001.
Sato-Nishimori, "Effects of Hochu-ekki-to added Yokuinin on Eczema in Childhood," *Japanese J. of Oriental Medicine*, 51(1): 7-14, 2000.

(Continued)

*Primary Examiner*—Michele Flood
(74) *Attorney, Agent, or Firm*—Finnegan, Henderson, Farabow, Garrett, & Dunner L.L.P.

(57) ABSTRACT

A method for prevention or therapy of pollen allergy, allergic rhinitis, atopic dermatitis, asthma or urticaria by administration of two kinds of crude drugs—seeds of *Cucurbita moschata* and flowers of *Carthamus tinctorius*—and at least one crude drug selected from *Plantago asiatica, Lonicera japonica, Glycyrrhiza uralensis, Coix lachrymal-jobi* var. *ma-yuen, Zingiber officinale, Curcuma longa, Curcuma zedoaria* and *Artemisia argyi* to a patient; and a health food for prevention, or improvement, or reduction of these symptoms containing the above substances.

2 Claims, 3 Drawing Sheets

OTHER PUBLICATIONS

Yano et al., "Antiallergic Activity of Extracts from *Curcuma longa* (4): Effect of Curcuminoids on Release of Inflammatory Mediators and Experimental Model for Atropic Dermatitis," *J. of Traditional Medicines*, 14: 430-431, 1997.

*Kampo no Rinsho*, 46(8): 1424-1429, 1999.

Shibata, "A Drug Over the Millennia: Pharmacognosy, Chemistry, and Pharmacology of Licorice," *Yakugaku Zasshi*, 120(10): 849-862, 2000.

Terasawa et al., "Four Cases Report of Atopic Dermatitis Succes[s-]ful[l]y Treated with Tokaku-Joki-To," *Nihon Toyo Igaku Zasshi (Japanese J. Oriental Medicine)*, 46(1): 45-54, 1995.

Okazaki et al., "Clinical Studies on the Kampo Preparation, Shoseityuto to Cases of Nasal Allergy," *Jibirinsho*, 7(3): 367-380.

"Therapeutic Effect of Coix Seed (Yokuinin) Extract Powder on Molluscum Contagiosum—Well-Controlled Double Blind Trials by Multi-Institutes Compared with Placebo," *Hihu*, 29(4): 762-773, 1987.

Inoue, Result Report (first phase): Fundamental Study of Inhibition of IgE Antibody Production by Functional Food, *Science and Technology Agency Research and Development Office*, 197-211, 2000.

Yamamoto, "Criticism of Juumihaidoku-to," *Kanpokenkyu*, 172(1): 143-151, 1986.

Muroi et al., "Antihistaminic Activity of Artemisiae Folium Extract and Its Clinical Effect on Pruritus Cutaneus," *Jpn. J. Hosp., Pharm.*, 20(1): 10-16, 1994.

* cited by examiner

Formulation A

Formulation B

PREVENTIVE OR THERAPEUTIC AGENT FOR POLLEN ALLERGY, ALLERGIC RHINITIS, ATOPIC DERMATITIS, ASTHMA OR URTICARIA, OR HEALTH FOOD FOR PREVENTION OR IMPROVEMENT OR REDUCTION OF SYMPTOMS THEREOF

This application is divisional of application Ser. No. 10/126,779, filed Apr. 22, 2002 now U.S. Pat. No. 6,811,796, incorporated herein by reference.

BACKGROUND OF THE INVENTION

1. Field of the Invention

The present invention is a preventive or therapeutic agent for pollen allergy, allergic rhinitis, atopic dermatitis, asthma or urticaria or a health food for prevention, improvement or reduction of symptoms thereof.

2. Description of the Related Art

In recent years, there has been a rapid increase in the number(s) of patients suffering from allergies caused by cedar pollen and by plants such as *Ambrosia artermisiifolia, Dactylis glomerata, Phleum pratense,* and birch or their pollen. In pollen allergies, chemical transmitters such as histamine and leukotriene and various enzymes are liberated from mast cells and basophils by pollen entering the body, and the typical symptoms of allergic conjunctivitis and allergic rhinitis (such as sniffles, stuffiness and sneezing) thereby appear, particularly in the nose and eyes.

There has been also an increase in allergic rhinitis, atopic dermatitis, asthma, urticaria, etc., caused not only by pollen, but also by house dust, ticks, etc., carrying allergens.

As a therapeutic countermeasure therefore, preventive therapy by anti-allergic agents has been carried out. This has consisted of a symptomatic treatment by new generation antihistaminic agents having fewer side effects on the nerves etc., orally administered agents such as various antagonists to chemical transmitters and inhibitors of the liberation of chemical transmitters, steroidal agents having a rapid pharmaceutical effect, and antihistaminic nasal drops having immediate effect and strong action, as well as hyposensitising therapy: etc. However, traditional Chinese drugs or antiallergic agents having a satisfactory effect in preventive therapy have yet to be found. In addition, with regard to antihistaminic agents and steroidal preparations, which are used in symptomatic treatment, their side effects often cause problems. In terms of therapy, it has been also reported that the degree of patients' satisfaction with the current status of treatment is extremely low. On the other hand, hyposensitizing therapy, while considered adequate by some, is beginning to show its limitations.

In U.S. Pat. No. 5,882,672, it is reported that when the seeds of one or more (preferably both) of the genera *Cucurbita moschata* and *Plantago asiatica,* and the flowers of *Lonicera japonica* are added to feed, natural infections by parasites, bacteria and viral diseases are largely prevented, the prophylactic force of living bodies is enhanced, and the flesh and ooplasm are improved. A feed in which two kinds of crude drugs composed of seeds, those of *Cucurbita moschata* and *Plantago asiatica,* and two kinds of crude drugs composed of flowers, those of *Lonicera japonica* and *Carthamus tinctorius,* were combined, was given to chickens to improve the quality of their eggs. Moreover, better health and survival rates, improvement in ooplasm and anti-leucocytozoonosis were observed. Further, in quail, the suppression of anti-Newcastle disease and enteric coccidium and a reduction in the incidence of the number of *Staphylococci* were also observed.

In U.S. Pat. No. 4,421,746, it is stated that an interferon inducer can be extracted from the plants of the genus *Cucurbitaceae,* such as Japanese pumpkin and, in U.S. Pat. No. 4,456,597, antiviral activity and anti-tumor activity of interferon inducers extracted from *Carthamus tinctorius* were also reported, leading to the conclusion that the inducer is useful as an anti-tumor agent and agent for the improvement of physiological action and general enhancement of health. In addition, in U.S. Pat. No. 4,469,685, it is reported that interferon inducers may be extracted from the flowers of *Lonicera japonica,* seeds of *Plantago asiatica,* etc., and are useful for the prevention of, and therapy, for viral infections in human beings and animals. In Japanese Patent Laid-Open No. 116,498/1999, a macrophage activator is described in which two crude drugs—seeds of *Cucurbita moschata* and flowers of *Carthamus tinctorius*—are combined and, in Japanese Patent Laid-Open No. 281,584/2000, a neutrophil activator wherein four kinds of crude drugs—seeds of *Cucurbita moschata,* flowers of *Carthamus tinctorius,* seeds or total plant of *Plantago asiastica,* and flowers of *Carthamus tinctorius* and *Lonicera japonica*—are combined, is described.

SUMMARY OF THE INVENTION

The present inventors have carried out an intensive investigation with the object of finding further specific uses of crude drugs such as the seeds of *Cucurbita moschata* and *Plantago asiatica,* and the flowers of *Carthamus tinctorius* and *Lonicera japonica,* etc., having such excellent effects as mentioned above. As a result, it has been found that a combination of two kinds of crude drugs—seeds of *Cucurbita moschata* and flowers of *Carthamus tinctorius*—with at least one crude drug selected from *Plantago asiatica, Lonicera japonica, Glycyrrhiza uralensis, Coix lachryma-jobi* var. *ma-yuen, Zingiber officinale, Curcuma longa, Curcuma zedoaria, Artemisia argyi,* etc., (particularly a combination of four crude drugs—seeds of *Cucurbita moschata* and *Plantago asiatica,* and flowers of *Carthamus tinctorius* and *Lonicera japonica*—or a combination of *Perilla frutescens* var. *crispa* with a combination of three crude drugs—seeds of *Cucurbita moschata,* flowers of *Carthamus tinctorius* and cereal of *Coix lachrymal-jobi* var. *ma-yuen*), have had excellent effects in the prevention of, or therapy for pollen allergy, allergic rhinitis, atopic dermatitis, asthma or urticaria. In addition, it is also very safe.

Thus, the present invention is a preventive or therapeutic agent for pollen allergy, allergic rhinitis, atopic dermatitis, asthma or urticaria, containing two kinds of crude drugs—seeds of *Cucurbita moschata* and flowers of *Carthamus tinctorius*—and at least one crude drug selected from *Plantago asiatica, Lonicera japonica, Glycyrrhiza uralensis, Coix lachrymal-jobi* var. *ma-yuen, Zingiber officinale, Curcuma longa, Curcuma zedoaria* and *Artemisia argyi,* as effective components. The present invention is also a preventive or therapeutic agent for pollen allergy, allergic rhinitis, atopic dermatitis, asthma or urticaria, containing four kinds of crude drugs—seeds of *Cucurbita moschata* and *Plantago asiatica,* and flowers of *Carthamus tinctorius* and *Lonicera japonica*—as effective components, or is a preventive or therapeutic agent for pollen allergy, allergic rhinitis, atopic dermatitis, asthma or urticaria, containing four kinds of crude drugs—seeds of *Cucurbita moschata,* flowers of *Carthamus*

*tinctorius*, cereal of *Coix lachrymal-jobi* var. *ma-yuen* and leaves of *Perilla frutescens* var. *crispa*—as effective components.

Further, the present invention is a method for the prevention of, or therapy for, pollen allergy, allergic rhinitis, atopic dermatitis, asthma or urticaria by administration of two kinds of crude drugs—seeds of *Cucurbita moschata* and flowers of *Carthamus tinctorius*—and at least one crude drug selected from *Plantago asiatica, Lonicera japonica, Glycyrrhiza uralensis, Coix lachrymal-jobi* var. *ma-yuen, Zingiber officinale, Curcuma longa, Curcuma zedoaria* and *Artemisia argyi*, to patients. The present invention is also a method for the prevention of, or therapy for pollen allergy, allergic rhinitis, atopic dermatitis, asthma or urticaria by administration of four kinds of crude drugs—seeds of *Cucurbita moschata* and *Plantago asiatica*, and flowers of *Carthamus tinctorius* and *Lonicera japonica*—to patients or is a method for the prevention of or therapy for, pollen allergy, allergic rhinitis, atopic dermatitis, asthma or urticaria by the administration of four kinds of crude drugs—seeds of *Cucurbita moschata*, flowers of *Carthamus tinctorius*, cereal of *Coix lachrymal-jobi* var, *ma-yuen* and leaves of *Perilla frutescens* var. *crispa*—to patients.

Furthermore, the present invention is a method for the prevention of pollen allergy by the administration of two kinds of crude drugs—seeds of *Cucurbita moschata* and flowers of *Carthamus tinctorius*—and at least one crude drug selected from *Plantago asiatica, Lonicera japonica, Glycyrrhiza uralensis, Coix lachrymal-jobi* var. *ma-yuen, Zingiber officinale, Curcuma longa, Curcuma zedoaria* and *Artemisia argyi*, to a person suffering every year from pollen allergy before the season for pollen allergy starts. The present invention is also a method for the prevention of pollen allergy by the administration of four kinds of crude drugs—seeds of *Cucurbita moschata* and *Plantago asiatica*, and flowers of *Carthamus tinctorius* and *Lonicera japonica*—to a person suffering every year from pollen allergy before the season for pollen allergy starts, or is a method for the prevention of pollen allergy by the administration of four kinds of crude drugs—seeds of *Cucurbita moschata*, flowers of *Carthamus tinctorius*, cereal of *Coix lachrymal-jobi* var. *ma-yuen* and leaves of *Perilla frutescens* var. *crispa*—to a person suffering every year from pollen allergy before the season for pollen allergy starts.

Still further, the present invention is a health food for the prevention or improvement or reduction of the symptoms of pollen allergy, allergic rhinitis, atopic dermatitis, asthma or urticaria containing two kinds of crude drugs—seeds of *Cucurbita moschata* and flowers of *Carthamus tinctorius*—and at least one crude drug selected from *Plantago asiatica, Lonicera japonica, Glycyrrhiza uralensis, Coix lachrymal-jobi* var. *ma-yuen, Zingiber officinale, Curcuma longa, Curcuma zedoaria* and *Artemisia argyi*. The present invention is also a health food for the prevention or improvement or reduction of the symptoms of pollen allergy, allergic rhinitis, atopic dermatitis, asthma or urticaria containing four kinds of crude drugs—seeds of *Cucurbita moschata* and *Plantago asiatica*, and flowers of *Carthamus tinctorius* and *Lonicera japonica*, or is a health food for the prevention or improvement or reduction of the symptoms of pollen allergy, allergic rhinitis, atopic dermatitis, asthma or urticaria containing four kinds of crude drugs—seeds of *Cucurbita moschata*, flowers of *Carthamus tinctorius*, cereal of *Coix lachrymal-jobi* var. *ma-yuen* and leaves of *Perilla frutescens* var. *crispa*.

Still furthermore the present invention is a health food for the prevention of the onset of pollen allergy containing two kinds of crude drugs—seeds of *Cucurbita moschata* and flowers of *Carthamus tinctorius*—and at least one crude drug selected from *Plantago asiatica, Lonicera japonica, Glycyrrhiza uralensis, Coix lachrymal-jobi* var. *ma-yuen, Zingiber officinale, Curcuma longa, Curcuma zedoaria* and *Artemisia argyi*. The present invention is also a health food for the prevention of the onset of pollen allergy containing four kinds of crude drugs—seeds of *Cucurbita moschata* and *Plantago asiatica*, and flowers of *Carthamus tinctorius* and *Lonicera japonica*, or is a health food for the prevention of the onset of pollen allergy containing four kinds of crude drugs—seeds of *Cucurbita moschata*, flowers of *Carthamus tinctorius*, cereal of *Coix lachrymal-jobi* var. *ma-yuen* and leaves of *Perilla frutescens* var. *crispa*.

In the above-mentioned U.S. patents and literature, interferon inducing action, macrophage activating action, neutrophil activating action, inhibiting action against IgE antibody production, etc., for each of the crude drugs which are the effective components of the present invention have been reported, but there is neither disclosure nor suggestion at all concerning the preventive or therapeutic effects on specific human diseases.

The present inventors have confirmed that the combination of the crude drugs as combined in the present invention significantly reduces the symptoms of the diseases or prevents the onset of the symptoms of patients suffering from pollen allergy, allergic rhinitis, atopic dermatitis, asthma or urticaria. They have further confirmed that the combination of the crude drugs in the present invention is very safe and that, even after administration for as long as six years, no side effects have been found, and that it is suitable for common use not only as a therapeutic agent, but also as a preventive agent, functional food dietary supplement or health food for long term administration.

In addition, its joint use with conventional therapeutic agents does not seem to show any bad influence on the therapy. Its joint use with currently used therapeutic agents in an auxiliary manner is thought to be possible.

The present invention will now be discussed in more detail as hereunder.

First, the crude drugs used in the present invention will be described.

Seeds of *Cucurbita moschata*, the genus *Cucurbitaceae* and, in the present invention, seeds of similar plants achieving the object of the present invention, are included herein as well. Although the seeds of *Cucurbita moschata* may be used in their raw state, dry seeds are preferred because of their superior keeping qualities as medicament and health food. It is also possible to use the seed coat only. Components include cucurbitin, protein and vitamins A, $B_1$, $B_2$ and C, and carotene, etc.

*Carthamus tinctorius* is of the genus *Compositae*, and its dried tubular flower is used. Carthamin, safflor yellow, lignan and sterol are among its components. It is used for the therapy of circulation disorders such as female reproductive disorders, sensitivity to the cold, menopausal disorders, etc.

*Plantago asiatica* is a member of the *Plantaginacea* and its matured seeds (shazenshi) or entire plant (shazen) are used. They contain polysaccharides, plantenolic acid, succinic acid, adenine, aucubin, plantaginin, vitamins A and $B_1$, etc. They are used as anti-inflammatory agents, diuretic agents and antidiarrheal agents in their crude forms.

*Lonicera japonica* is of the genus *Gramineae* and its flower or bud, leaf, stem or entire plant is used. It contains inositol, tannin, saponin, lonicerin, etc., as components. It is used as an antipyretic agent, poison antidote, diuretic agent, anti-inflammatory agent, etc., in its crude form.

*Glycyrrhiza uralensis* is one of the *Leguminosae* and its dried root and rhizome are used. Its main medicinal component is glycyrrhizin. It is used as an alleviant, remitting agent, antitussive agent, analgesic agent and expectorant in its crude form.

*Coix lachrymal-jobi* var. *ma-yuen* is of the *Gramineae* and its cereal is used. It contains fatty oil as one of its components and in the oil coixenolide, coixol, amino acids, vitamin $B_1$ and saccharides are contained. It is used as a cancer cell suppressor, antipyretic agent, sedative, tranquilizer and hypoglycemic agent in its crude form.

*Zingiber officinale* is one of the *Zingiberaceae* and its dried rhizome is used. As raw ginger, the same effect is possible, although dried ginger is preferred as a medicament and health food in view of its preservability. It contains essential oils and gingerol. It is used for improvement of blood circulation, hypertension, the excitation of vasomotor centers, and excitation of sympathetic nerves in its crude form.

*Curcuma longa* is of the genus *Zingiberaceae,* and its rhizome is used. It contains curcumin, and essential oils etc., among its components. It is used as a cholagogue, hypotensive agent, antibacterial agent sedative, etc., in its crude form.

*Curcuma zedoaria* is of the *Zingiberaceae* and its rhizome is used. It contains curcumin, essential oils, etc., as the main components. It is used as an anti-tumor agent, antibacterial agent and stomachic agent in its crude form.

*Artemisia argyi* is a member of the *Compositae* and its dried leaves are used. It contains essential oils and vitamins A, B, C and D as the main components. It is used as an antibacterial agent, agent for stopping bleeding and shortening blood coagulation time, antitussive agent, expectorant, anti-inflammatory agent, appetite promoter, etc., in its crude form.

The therapeutic agent and the health food form of the present invention contains two kinds of crude drugs—seeds of *Cucurbita moschata* and flowers of *Carthamus tinctorius*—and at least one crude drug selected from *Plantago asiatica, Lonicera japonica, Glycyrrhiza uralensis, Coix lachrymal-jobi* var. *ma-yuen, Zingiber officinale, Curcuma longa, Curcuma zedoaria* and *Artemisia argyi* as effective components; the particularly preferred form is a compound of four kinds of crude drugs, .e.e., seeds of *Cucurbita moschata* and *Plantago asiatica,* and flowers of *Carthamus tinctorius* and *Lonicera japonica*. A combination of three kinds of crude drugs—seeds of *Cucurbita moschata,* flowers of *Carthamus tinctorius* and cereal of *Coix lachrymal-jobi* var. *ma-yuen*— to which *Perilla frutescens* var. *crispa* is supplemented, is preferred as well.

In the present invention, these crude drugs may be used as crude powder or as an extract with water or organic solvents. Thus, they are used as crude powder, solvent preparation, powdery preparation, molded preparation, exudate, etc. With regard to the organic solvents, alcohol, acetone, etc., may be used and extraction may be accomplished using a mix of two or more kinds of organic solvents. In the extraction, several times as much solvent is added to the crude drug, and the extraction or extrusion is carried out at ambient temperature or with heating. The extracted essence of each crude drug may be extracted individually and then mixed or the essence may be extracted from pre-mixed fresh herbs. When a crude drug is used, it may be in its fresh/crude form, after drying in the shade, or after drying and then finely cutting or powdering.

The above-mentioned powder of crude drug or extract with water or with organic solvent may be utilized as health food, functional food or dietary supplement or medicament as it is, or after making into various forms by a method well known.

For example, medicament or functional food or dietary supplement may be provided in the form of tablets, diluted powder, fine granules, capsules, pills or syrup for oral use by means of a conventional method of preparation. For making into preparations, it is possible to add fillers, binders, disintegrating agents, lubricants buffers, corrigents, stabilizers, etc., thereto. At least one inert diluent such as lactose, mannitol, glucose, hydroxypropyl cellulose, finely crystalline cellulose, starch, polyvinylpyrrolidone or magnesium metasilicate aluminate is mixed therewith. In addition to the inert diluents, the composition may contain additives such as lubricants (e.g., magnesium stearate, starch and talc), disintegrating agents (e.g., calcium cellulose glycolate), stabilizers (e.g., lactose) and solubilizing aids (e.g., glutamic acid and aspartic acid) in accordance with conventional methods. Tablets or pills may be coated, if necessary, with a sugar coat such as sucrose, gelatin, agar, pectin, hydroxypropyl cellulose, hydroxypropyl methyl cellulose, etc., or with the film of a substance which is soluble in the stomach or in the intestine.

To such an extent that the crude drug which is the effective component of the present invention is not affected, it to also possible to further combine it with caffeine, water-soluble vitamins such as vitamin $B_1$, vitamin $B_2$, vitamin $B_6$, vitamin $B_{12}$, vitamin C, biotin, carnitine, pantothenic acid, nicotinic acid and derivatives thereof, fat-soluble vitamins such as vitamin A, vitamin E and derivatives thereof, and amino acids such as taurine and arginine. It is further possible that oriental herbs (such as licorice root, ginkgo, dandelion, chrysanthemum flower, carrot, cinnamon, etc.) or western herbs (such as *Serenoa repens, Hypericum perforatum,* echinacea, aniseed, annual chamomile (chamomile), rosemary, mint, eucalyptus, lavender, rose, hibiscus, aloe, etc.) may be added in a supplementary manner. It is also preferred to combine the crude drug with *Perilla frutescens* var. *crispa,* which has been reported to be particularly effective for pollen allergy, allergic rhinitis and atopic dermatitis (*FOOD Style,* 21, 2(4), 50-54, 1998) in a (n) supplementary manner.

Liquid compositions for oral use contain a pharmaceutically acceptable emulsion, solution, suspension, syrup, elixir, etc., and contain a commonly used inert diluent such as pure water or ethanol. In addition to the inert diluent, the composition may also contain a moisturizer, an auxiliary agent such as a suspending agent sweeteners, flavor agents, aromatic agents and antiseptic agents.

In the case of health food, it is possible to provide the compound in the form of a beverage or confection such as a jelly, biscuit, cookie, candy, etc.

The present invention consists of seeds of *Cucurbita moschata,* flowers of *Carthamus tinctorius,* and at least one kind of crude drug from the following: *Plantago asiatica, Lonicera japonica, Glycyrrhiza uralensis, Coix lachrymal-jobi* var. *ma-yuen, Zingiber officinale, Curcuma longa, Curcuma zedoaria* and *Artemisia argyi,* as effective ingredients. Moreover, it is more effective when this invention contains seeds of *Cucurbita moschata* in a percentage of from 20% to 60%, a percentage of flowers of *Carthamus tinctorius* from 10% to 40%, and each of the other crude drugs listed from 5% to 50%.

The combination of crude drugs according to the present invention may be appropriately determined for each case, taking age, gender, etc., of the subject into consideration. Usually, when 0.5-2 g or, preferably a total amount of 1 g of the crude drugs a day to a 60 kg adult is orally administered; the desired therapeutic or preventive effect can be achieved without any side effects.

The combination of crude drugs according to the present invention can be used not only as a preventive/therapeutic agent and health food for humans, but also as a therapeutic agent and health food for the improvement/reduction of health problems in pets such as dogs and cats.

DETAILED DESCRIPTION OF THE PREFERRED EMBODIMENTS AND EXAMPLES

Figure 1:
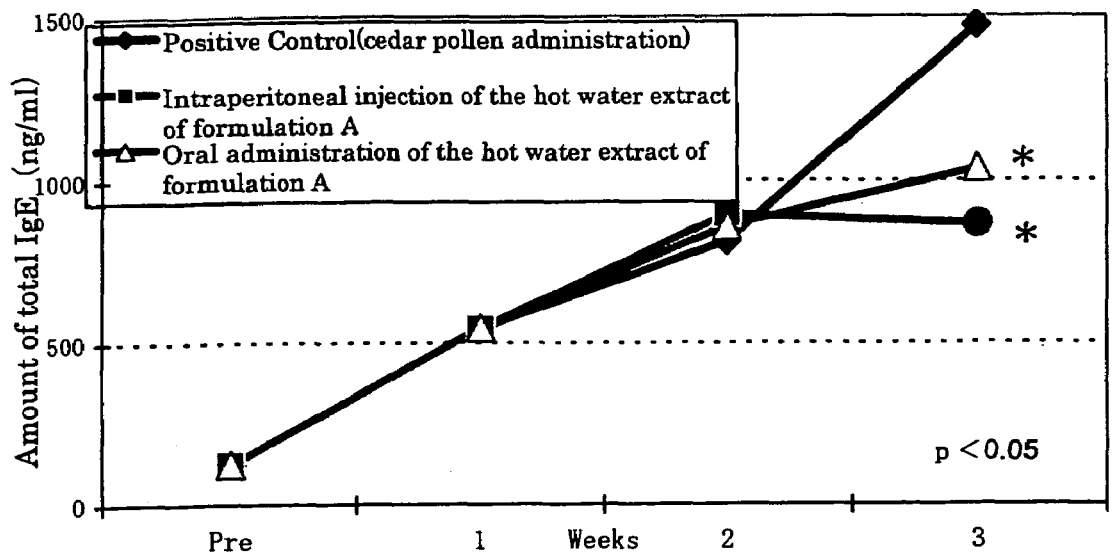
FIG. 1 shows the total amount of IgE antibodies in the blood produced in response to cedar pollen in a mouse to which the hot water extract of formulation A was orally administered or intraperitoneally injected.

As hereunder, the present invention will be illustrated in more detail by way of Examples and Test Examples, although the present invention is not limited to those Examples, etc.

EXAMPLE 1

Health Food

Powder of crude drugs having the combined components of the following formulation A or formulation B was mixed and extracted using a 10-fold amount of water at 95±5° C. for 30 minutes, the extract was filtered and concentrated, then fillers such as reducing maltose, lactose, starch, etc., and scent were added thereto and the mixture was subjected to a granulating step to produce fine granules.

Formulation A components ratio: seeds of *Cucurbita moschata* (50%) and *Plantago asiatica* (15%), and flowers of *Carthamus tinctorius* (20%) and *Lonicera japonica* (15%)

Formulation B components ratio: seeds of *Cucurbita moschata* (40%), flowers of *Carthamus tinctorius* (20%), cereal of *Coix lachrymal-jobi* var. *ma-yuen* (20%) and leaves of *Perilla frutescens* var. *crispa* (20%)

TEST EXAMPLE 2

Inhibiting Production of Total IgE Antibodies in the Blood of Mice Sensitized with Cedar Pollen BALB/cCrSlc mice (female) of 12-15 weeks age were used. Inhibiting action on the production of total IgE antibodies in the blood in response to cedar pollen ((Cedar Pollen Extract-Cj) (LSL Co., Ltd.)) when the hot water extract of formulation A was orally administered or intraperitoneally injected, was investigated. The extract for the oral administration group was prepared by adding a 10-fold amount of water to the original crude drugs of formulation A. Extraction was carried out at 95±5° C. for 30 minutes. The extract was continuously centrifuged at 900×g; the supernatant liquid thereof was further centrifuged at 10,000×g and the supernatant liquids were combined to produce the extract. The extract for the Intraperitoneal injection group was prepared by adding a 10-fold amount of water to the original crude drugs of formulation A. Extraction was carried out at 95±5° C. for 30 minutes. The extract was continuously centrifuged at 900×g; the supernatant liquid thereof was further centrifuged at 10,000×g and the supernatant liquids were combined. These supernatant liquids were dialyzed to collect a fraction having a molecular weight of 14,000 or more, then filtered through a 0.45 MY Filter and sterilized, resulting in an extract. The test groups were as follows.

Group 1: a non-treated control (negative control group)

Group 2: a group to which pollen was given

Group 3: a group to which pollen and extract for intraperitoneal infection (0.3 ml) were given Group 4: a group to which pollen and extract for oral administration (0.6 ml) were given The method for the measurement of the total number of IgE antibodies was in such a manner that all the blood was collected under anesthetization and the sample serum was separated and preserved at −80° C. until the antibody value was measured. A sandwich ELISA method carried out measurement of the total number of IgE antibodies in the conventional manner.

Results of the measurement of the total number of IgE antibodies are shown in FIG. 1. Before administration and in the first and second weeks, there was no significant difference among the groups. However, in the third week there was a significant increase to 1474.2 ng/ml in the group to which only pollen was given (group 2), while, in the group where pollen and intraperitoneal injection were applied (group 3) (866.97 ng/ml) and in the group to which pollen and oral administration were applied (group 4) (1036.24 ng/ml), the increase was significantly inhibited as compared with the group where only pollen was administered (group 2) ($p<0.05$ in a student's t-test). In a comparison between the group where pollen and intraperitoneal injection were applied (group 3) and the group where pollen and oral administration were applied (group 4), there was no statistical Significance.

From the above results, it was confirmed that the health food containing the present invention inhibited the production of IgE antibodies in the blood of mice sensitized with cedar pollen and was able to inhibit the allergic reaction.

TEST EXAMPLE 2

Preventive or Therapeutic Effects on Patients Suffering from Cedar Pollen Allergy In order to investigate the efficacy and the safety of health food containing the present invention with regard to pollen allergy, a clinical test was carried out with male and female adult patients suffering from pollen allergy, using the hot water extracts of formulations A and B, as used in Example 1. Formulation A was applied to 20 patients suffering from pollen allergy (10 males and 10 females) while formulation B was given to 72 patients suffering from pollen allergy. The test was started early in February and administration was begun individually by each patient on his/her own and continued for 90 days. The patients were asked to fill in questionnaires before the start and at the time of completion, and evaluation was carried out in accordance with the answers given. During the test, the hot water extract containing essence equivalent to that found in 1.0 g of the original crude drugs was administered during the test period, administration being recorded every day. Any subject who stopped his treatment during the administration period or who took the food irregularly was excluded from the final evaluation of the effects.

Figure 2:
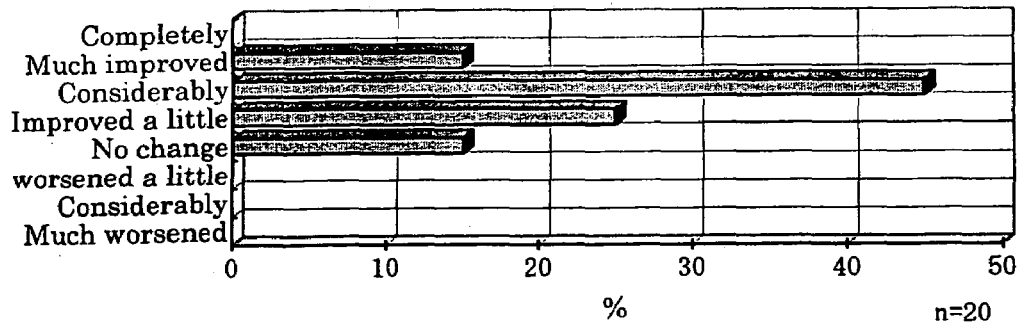
FIG. 2 shows the evaluation of the degree of improvement in patients suffering from pollen allergy effected by the hot water extracts of formulation A and formulation B in Example 1.
Figure 2:
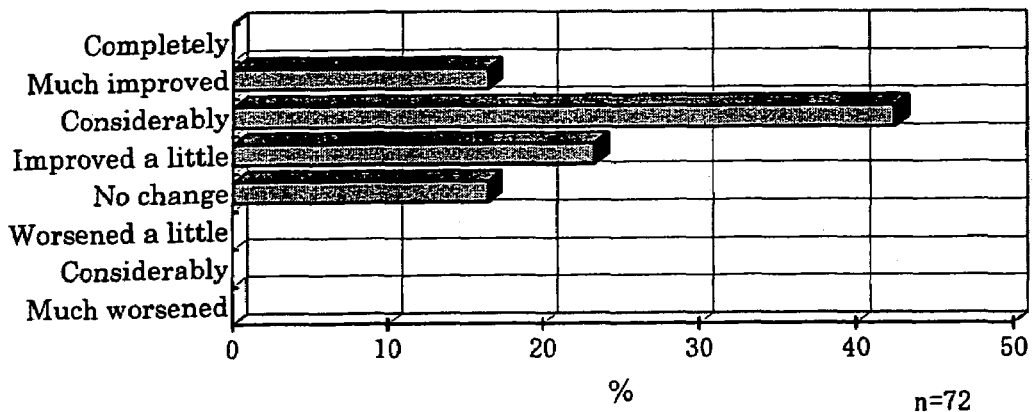

After the test, the patients were ask to report their degree of improvement as compared with their usual symptoms during that season in terms of eight stages: completely cured, much improved, considerably improved, improved a little, no change, worsened a little, considerably worsened and much worsened. The result was that, in both formulations A and B, one-half or more of the subjects were "considerably improved" or better, and more than 80% were "improved a little" or better (FIG. 2).

Figure 3:
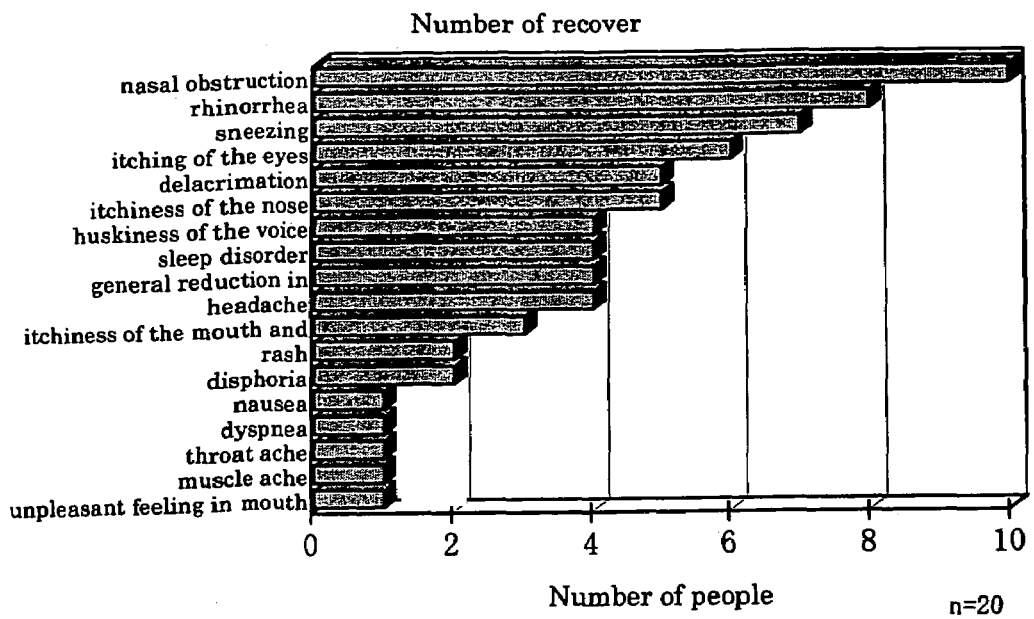
FIG. 3 shows symptoms improved by the hot water extract of formulation A as per Example 1.

When the usual symptoms of every preceding year until now, and those of this year were compared for the patients to whom the hot water extract of formulation A was administered, an improvement in the symptoms in nasal obstruction, rhinorrhea, sneezing, itching of the eyes, delacrimation, itching of the nose, huskiness of the voice, sleeping disorders, general reduction in symptoms from previous years, headaches, itching of the mouth and throat, rash, disphoria, nausea, dyspnea, throat ache, muscle ache and unpleasant feeling in the mouth, was noted (FIG. 3).

Figure 4:
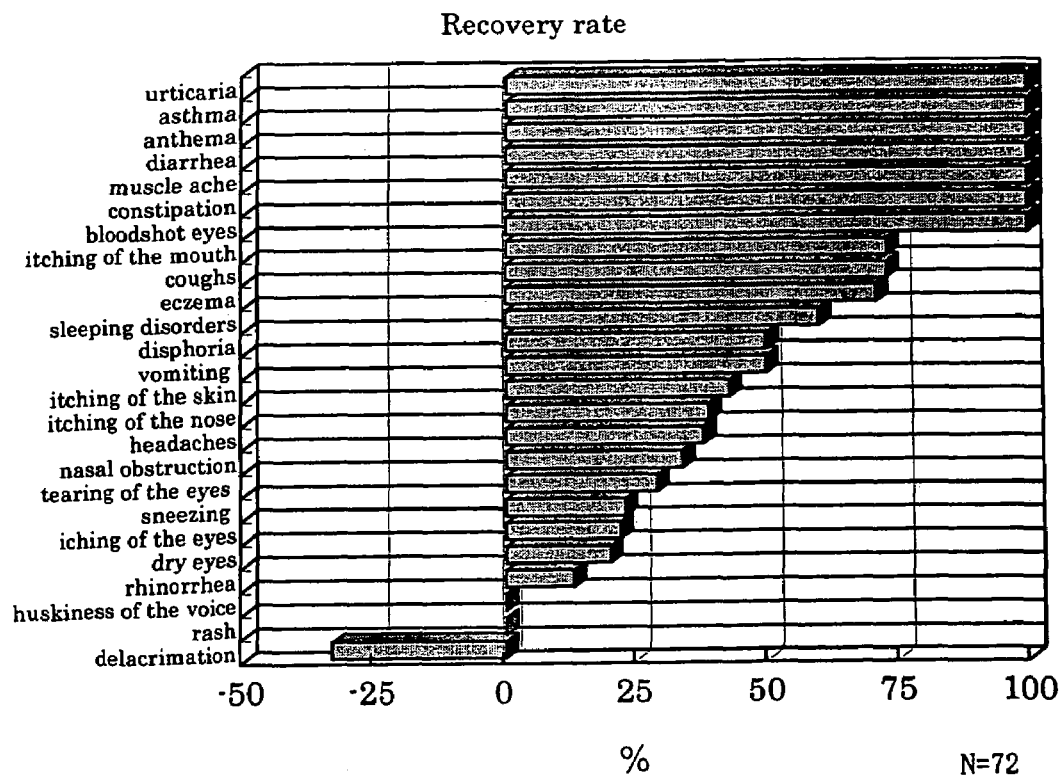
FIG. 4 shows symptoms improved by the hot water extract of formulation B as per Example 1.

When the usual symptoms experienced in previous years and those of this year were compared for the patients to whom the hot water extract of formulation B was administered improvement was noted in 100% of the patients for the symptoms of urticaria, asthma, anthema, diarrhea, muscular ache, constipation and bloodshot eyes, and an improvement in many was noted for (in order of the number improved) itching of the mouth and throat, coughs, eczema, sleeping disorders, disphoria, vomiting, itching of the skin, itching of the nose, headaches, nasal obstruction, tearing of the eyes, sneezing, itching of the eyes, dry eyes and rhinorrhea (FIG. 4).

Figure 5:
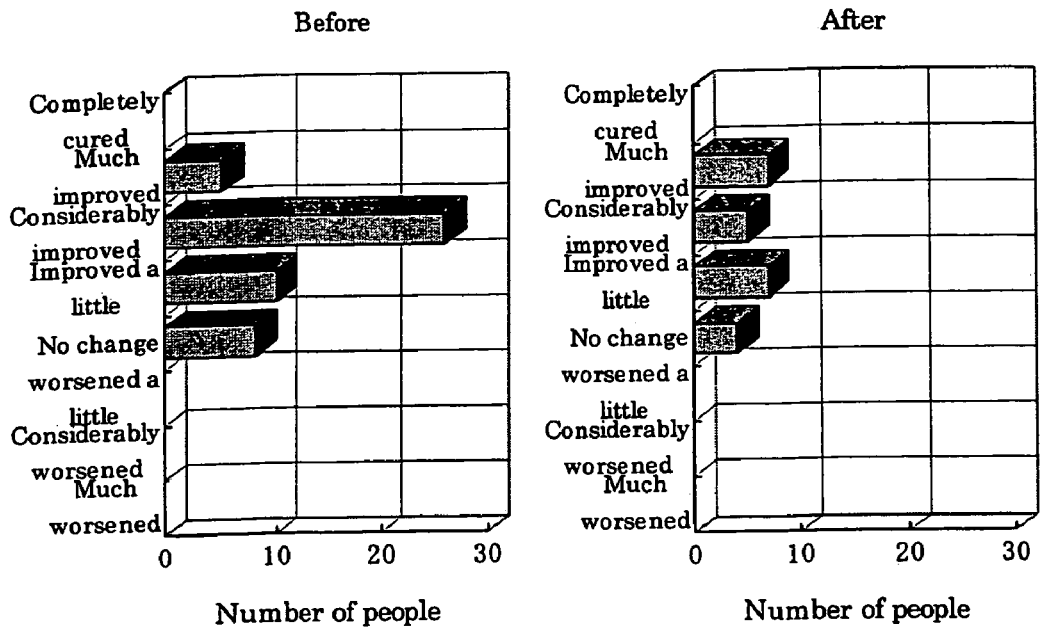
FIG. 5 shows the correlation between the degree of improvement in the symptoms and the time of the start of administration of the hot water extract of formulation B as per Example 1.

The analysis of the correlation of improvement in symptoms and the starting time of treatment with the hot water extract using formulation B, showed that when administration was started from a stage before the onset of symptoms (early February), more cases were "considerably improved" or better, than where administration was started after the onset of symptoms (FIG. 5). Accordingly, it was confirmed that the combined crude drugs of the present invention had a preventive therapeutic effect.

Figure 6:
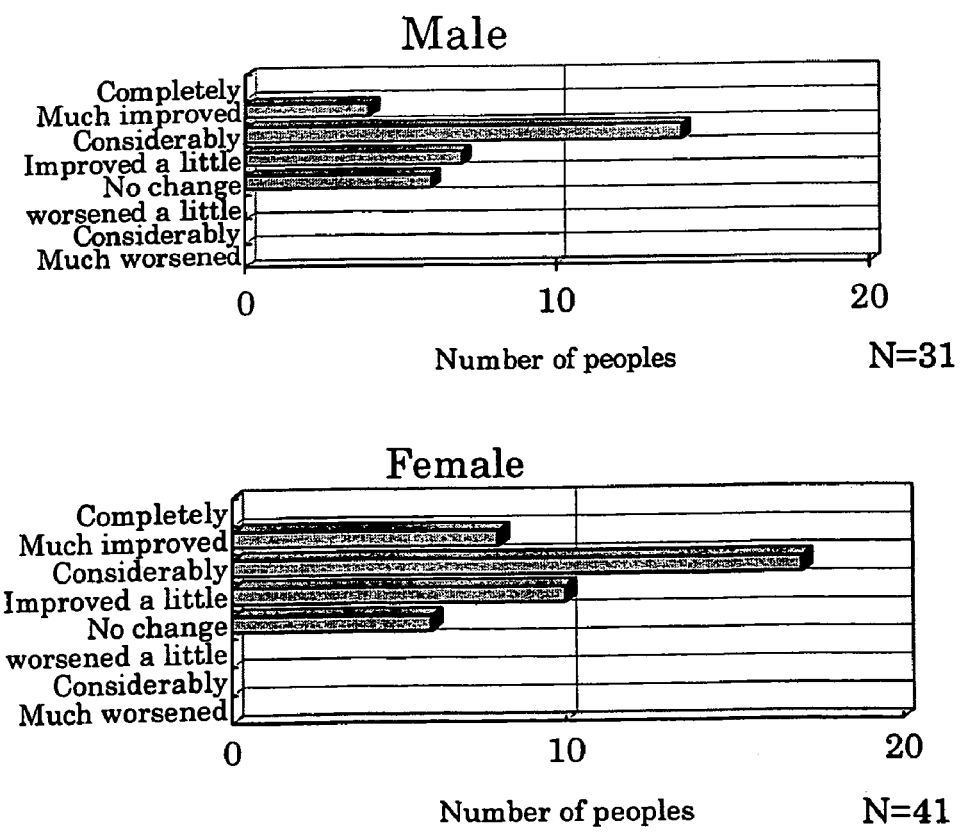
FIG. 6 shows degrees of improvement by gender of the patients taking the hot water extract of formulation B as per Example 1.

In the degree of improvement of the patients to whom the hot water extract of formulation B was administered, no influence due to the gender of the subject was noted (FIG. 6).

When a comparison was made between instances of joint use with therapy by the doctors, other medicament or other health foods, and instances where only the health food in which the formulation under discussion was used throughout, the degree of improvement was nearly the same, so it is likely that, even when used in combination with other therapeutic approaches, there were no bad effects. In addition, No influence on the degree of improvement by differences in body type was noted.

From the above-mentioned results, it was confirmed that the health food containing the present invention was effective in improving the symptoms of patients suffering from pollen allergies and that, especially when it was taken in a preventive manner before the start of the season, the onset of symptoms could be inhibited.

TEST EXAMPLE 3

Preventive Effects on Patients Suffering from Pollen Allergies

Health food using formulation A as in Example 1 (corresponding to 1 g of the crude powder per day) was given during 2 months beginning in early March to a female patient of 66 years age suffering from pollen allergy and an improvement in the symptom was observed. She was usually troubled by sniffles and itching of the eyes every year. She was given the medicaments ambroxol hydrochloride and progesterone together with the health food, and no symptoms of pollen allergy were noted during that period.

TEST EXAMPLE 4

Therapeutic Effects on Patients Suffering from Nasal Allergy

In order to investigate the efficacy and safety of the health food using the present invention with regard to nasal allergy, a single blind comparative test was carried out on patients suffering from a year-round nasal allergy using the health food containing formulation B in Example 1 and a placebo having the same appearance and taste as the health food above. In the test, 53 patients suffering from year-round house dust (HD) nasal allergy (18 years age and older were tested, with a proviso that no other medicament be jointly used). The diagnosis was carried out in such a manner that, in accordance with the guidelines for diagnosis of nasal allergy (Guidelines for Treatment of Nasal Allergy—Year-round Rhinitis—Revised Third Edition (1999)—by the Nasal Allergy Diagnosis Guideline Preparation Committee), those who were suffering from sneezing, sniffling and stuffiness, and being positive for two or more of the following: snivel acidophil test, HD intracutaneous reaction, blood HD RAST value and HD nasal induction test were defined as patients suffering from a throughout-the-year nasal allergy. Patients having the risk of being affected by pollen allergies during the administration period were excluded. In terms of classification according to the degree of severity of the symptoms, there were 25 light patients, 28 medium patients and 8 severe patients. After a control observation period of one week, either the actual treatment or a placebo was administered twice daily for 4 weeks (for each administration, a dosage corresponding to 1.0 g of original crude drugs was used) and the progress of the symptoms was judged from the allergy diaries of the patients. Before and after the administration, a peripheral blood test, hepatic and biliary system, renal function and urine tests were carried out to evaluate whether or not there were side effects. With regard to 18 patients to whom the treatment was administered in December, peripheral blood was collected before and after the administration, and erythrocytes were removed therefrom. Stimulation was applied with a tick antigen (10 ng/ml) to 24 plates, IL-5 and IFNγ in the supernatant liquid of the incubation solution after 7 days were measured by ELISA and, from a comparison with IL-5 and IFNγ in non-stimulated supernatant liquid after incubation, the amount of production of HD-stimulated IL-5 and IFNγ was determined.

After administration of the health food containing the formulation, there were no subjects who stopped treatment and investigation was possible for the 30 patients using the actual treatment and 23 patients using a placebo. Between the actual treatment group and the placebo group, there was no difference in the classification of the severity. Judging the degree of improvement from the patients' allergy diaries, there was an onset of sneezing in 20.0% of the actual treatment group and 30.4% of the placebo group; onset of sniffling was 16.6% in the actual treatment group and 39.1% in the placebo group; onset of stuffiness was 20.0% in the actual treatment group and 30.4% in the placebo group, and daily activities became more difficult in 6.6% of the actual treatment group and 13.0% of the placebo group, so that in all cases the actual treatment group was superior. Expression of significant side effects such as gastrointestinal symptoms was not noted in either actual treatment or placebo groups. Further, there was no abnormal data in the general blood tests.

Investigation of production of cytokine using peripheral blood was carried out on 11 patients for the actual treatment group and 7 patients for the placebo group with regard to IFN-γ while, with regard to IL-5; it was carried out on 6 patients in the actual treatment group and 6 patients In the placebo group. In the actual treatment group, production of IFN-γ caused by HD stimulation significantly increased after administration of the formulation, as compared with IFN-γ production before administration (p<0.05), while, in the placebo group, no significant change was noted. Production of IL-5 caused by HD stimulation significantly decreased (p<0.05) in the group using the formulation while, in the placebo group, only a slight but not significant decrease was noted. Accordingly, it was strongly suggested that health food using the present invention had a Th1 cytokine promoting action and a Th2 cytokine suppressing action.

From the above result, it was confirmed that health food using the present invention was effective for the improvement of symptoms of patients suffering from HD induced nasal allergy, and was safe as well. Its main action is believed to be an adjustment and improvement in an abnormal balance between Th1 and Th2 cytokines, which is a cause of type, I anaphylaxis.

TEST EXAMPLE 5

Therapeutic Effects on Patients Suffering from Year-Round Nasal Allergy

Health food using formulation A in Example 1 (corresponding to 1 g of the original crude drug per day) was administered to a male patient 4 years of age suffering from a year-round nasal allergy, and improvement in the symptoms was observed. In the initial stage, severe stuffiness was noted, but after the administration, much nasal mucus was discharged and the stuffiness was reduced. When the administration was stopped, his nose became stuffy again after one week.

TEST EXAMPLE 6

Therapeutic Effects on Atopic Dermatitis

Health food using formulation A in Example 1 (corresponding to 1 g of the original crude drug per day) was administered to a female patient of 27 years' age suffering from atopic dermatitis and improvement in the dermal symptoms was observed. Until that time, the patient had undergone therapy that included medicament, the intake of food devoid of allergens, and other health foods, but no apparent improvement in the symptoms was noted. When an observation was made after about one month from the beginning of administration of health food using the formulation, flaring of the skin, exudations, itching, etc., were reduced.

From the above results, it was confirmed that the health food of the present invention was effective in producing reductions in the symptoms of Atopic dermatitis.

TEST EXAMPLE 7

Therapeutic Effects on Infantile Asthma

Health food containing formulation A in Example 1 (corresponding to 1.5 g of the original powder per day) was administered to a male patient of 7 years age suffering from infantile asthma and improvement in the symptoms was observed. Until that time, therapy had been done by medicament, but when he was exposed to dust; symptoms of asthma were immediately noted. After the administration of health food containing the formulation however, his cough decreased and stuffiness was considerably diminished.

TEST EXAMPLE 8

Therapeutic Effects on Urticaria

After an abortion a half-year previously a female patient of 23 years age complained of map-like urticaria on the soft areas of the skin, mostly on the abdomen, hands and feet, every night. However, when health food using formulation A in Example 1 (three times a day; each corresponding to 1.0 g of crude powder) was administered and the symptoms were observed for six months, little by little a reduction in the symptoms during the period of administration was noted.

TEST EXAMPLE 9

Test for Confirmation of Safety

Safety of the health food in Example 1 was investigated in humans.

Health food containing the formulation was administered twice daily (corresponding to 1.0 g of crude drugs per administration) to 7 healthy and normal male adults. Before starting the administration, and after one and then two weeks from the start, blood was collected and general clinical tests (i.e. hematological tests, leukocyte numbers, erythrocyte numbers, hemoglobin amount, hematocrit value, MCV, MCH, MCHC, platelet numbers and differential white blood count), biochemical tests of blood (total protein, albumin, A/G, total bilirubin, MCV, MCH, MCHC, GOT, GPT, alkaline phosphatase, γ-GTP, total cholesterol, neutral fat, urea nitrogen, uric acid and creatinine), immunobiochemical tests (nonspecific IgE, nonspecific IgG and transferrin) and auscultation, percussion and physical tests (body temperature, pulse and blood pressure) were carried out by medical doctors whereby the safety of the health food of the present invention was investigated. The subjects were also interviewed. In addition, cell functions (macrophage devouring ability, neutrophil devouring ability and NK cell activity) and cytokines (IL-2, 4, 6, 8, 10, 12, INF-β and TNP-α) were measured whereby the efficacy of the present health food was determined.

The result was that, during the two-week period of test administration, no harmful cases seemingly caused by administration of the tested food were noted in subjective symptoms, objective findings and clinical test data, including immunobiochemical tests. It was confirmed that the health foods in Example 1 were of no problem in both formulations, A and B. With regard to cell function and cytokines, no significant changes were noted and, in healthy and normal male adults, it was found that there was no measurable harmful effect at the dosage level given during the administered terms.

TEST EXAMPLE 10

Safety as Health Food

Health food of the present invention was given to a healthy and normal male adult for six years. At the initiation of the administration, he was 31 years of age. During the first two years, a compound of crude drug powder of formulation A was given at a dose of 1 g on average per day and, after that, health food containing formulation A was given at a dose equivalent to 1 g of the original powder on average per day. The result was that, during the period of administration, no negative health effects were noted in general blood properties and state of health.

TEST EXAMPLE 11

Safety When used During Pregnancy

Health food of the present invention containing formulation B was administered to a female of 29 years' age during pregnancy and no ill effects on her state of health were noted during pregnancy, and upon and after delivery. The newborn male baby was also normal and has been growing in a healthy state subsequently.

INDUSTRIAL APPLICABILITY

In accordance with the present invention, there is provided a safe and excellent therapeutic agent for pollen allergy, allergic rhinitis, atopic dermatitis, asthma or urticaria of humans and companion animals. Especially for pollen allergy, it can be used as a preventive agent which is able to inhibit the onset of symptoms when administered before the season and thereafter. In addition, there is no risk of side effects and it can be commonly used for a long period, not only as medicament, but also as a functional food, dietary supplement or health food.

The invention claimed is:

1. A method of therapy for reducing the likelihood of the onset of symptoms in a patient suffering from pollen allergy, comprising administering to the patient before a season for pollen allergy an effective amount of a composition comprising a water extract from seeds of *Cucurbita moschata*, a water extract from flowers of *Carthamus tinctorius*, a water extract from seeds of *Plantago asiatica*, and a water extract from flowers of *Lonicera japonica*.

2. The method of claim 1, wherein the composition further comprises at least one extract from *Glycyrrhiza uralensis, Coix lachrymal-jobi* var. *ma-yuen, Zingiber officinale, Curcuma longa, Curcuma zedoaria*, or leaves of *Artemisia argyl*.

* * * * *

UNITED STATES PATENT AND TRADEMARK OFFICE
CERTIFICATE OF CORRECTION

| | | |
|---|---|---|
| PATENT NO. | : 7,452,557 B2 | Page 1 of 1 |
| APPLICATION NO. | : 10/964750 | |
| DATED | : November 18, 2008 | |
| INVENTOR(S) | : Satoshi Yoshida | |

It is certified that error appears in the above-identified patent and that said Letters Patent is hereby corrected as shown below:

In claim 2, column 14, line 25, "*argyl.*" should read --*argyi.*--.

Signed and Sealed this

Twenty-fourth Day of February, 2009

JOHN DOLL
*Acting Director of the United States Patent and Trademark Office*